United States Patent [19]

Puskas et al.

[11] Patent Number: 4,476,242

[45] Date of Patent: Oct. 9, 1984

[54] PROCESS FOR PREPARING PALLADIUM ON CARBON CATALYSTS FOR PURIFICATION OF CRUDE TEREPHTHALIC ACID

[75] Inventors: Imre Puskas, Wheaton; Steven A. Cerefice, Naperville, both of Ill.

[73] Assignee: Standard Oil Company (Indiana), Chicago, Ill.

[21] Appl. No.: 507,707

[22] Filed: Jun. 23, 1983

Related U.S. Application Data

[63] Continuation-in-part of Ser. No. 316,300, Oct. 29, 1981, abandoned.

[51] Int. Cl.$^3$ .................. B01J 23/44; C07C 51/42
[52] U.S. Cl. .................. 502/185; 562/487
[58] Field of Search .................. 502/185

[56] References Cited

U.S. PATENT DOCUMENTS

| 2,930,765 | 3/1960 | Cooper et al. | 252/447 |
| 4,093,559 | 6/1978 | Fernholtz et al. | 252/447 |
| 4,239,653 | 12/1980 | Bodnar et al. | 252/447 |
| 4,256,609 | 3/1981 | Dale et al. | 252/466 |
| 4,260,829 | 4/1981 | Horner et al. | 568/462 |
| 4,394,299 | 7/1983 | Puskas et al. | 502/185 |
| 4,415,479 | 11/1983 | Puskas et al. | 502/185 |
| 4,421,676 | 12/1983 | Puskas et al. | 502/185 |

FOREIGN PATENT DOCUMENTS 2936362 4/1981 Fed. Rep. of Germany ...... 252/447

Primary Examiner—P. E. Konopka
Attorney, Agent, or Firm—William C. Clarke; William T. McClain; William H. Magidson

[57] ABSTRACT

A catalyst, a process for preparing said catalyst, and a process for producing purified terephthalic acid, wherein 4-carboxybenzaldehyde is reduced to very low levels, wherein said catalyst is prepared by contacting a solution of a suitable palladium salt in an organic solvent with a suitable activated carbon support, wherein said palladium salt is reduced to palladium metal crystallites by said activated carbon support. Purified terephthalic acid is prepared by hydrogenating crude terephthalic acid in the presence of said catalyst.

9 Claims, 1 Drawing Figure

PALLADIUM DISTRIBUTION ACROSS A CARBON GRANULE BY ELECTRON MICROPROBE ANALYSIS

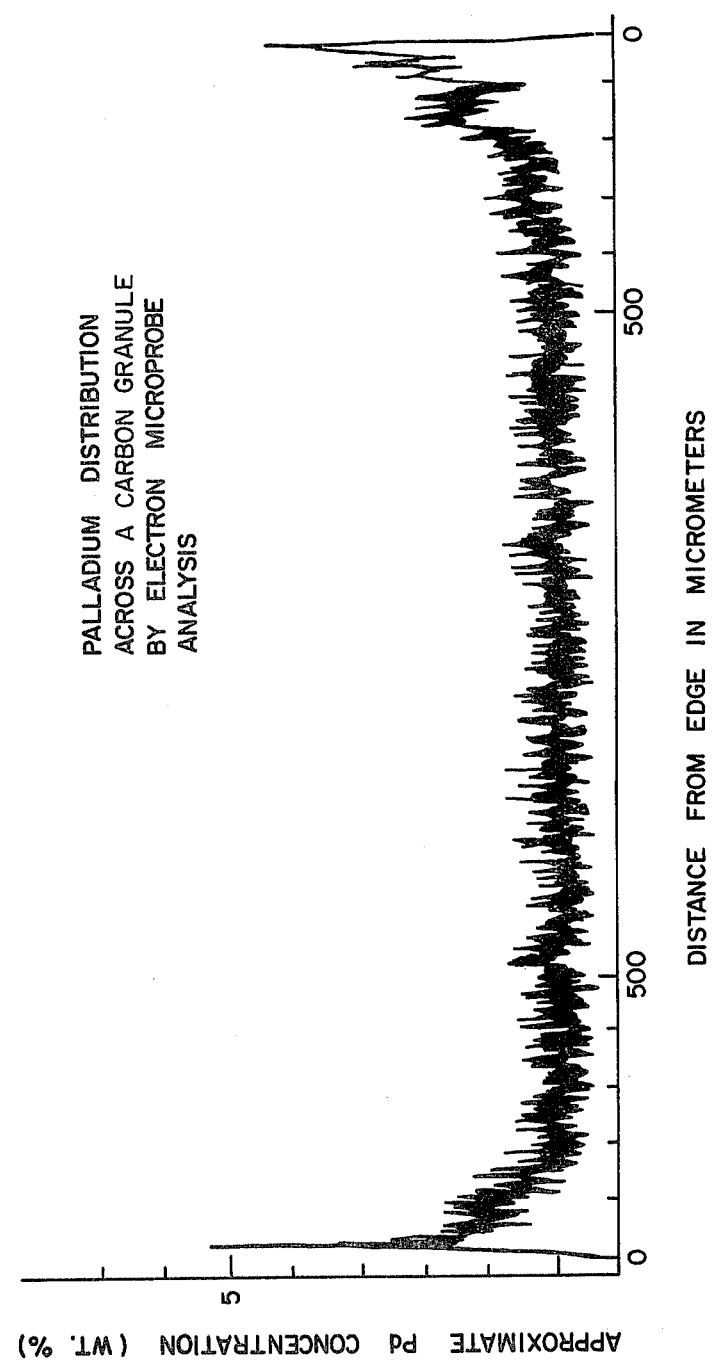

PROCESS FOR PREPARING PALLADIUM ON CARBON CATALYSTS FOR PURIFICATION OF CRUDE TEREPHTHALIC ACID

This application is a continuation-in-part of Ser. No. 316,300, filed Oct. 29, 1981 now abandoned.

BACKGROUND OF THE INVENTION

Purification of crude terephthalic acid by hydrogenation over a suitable catalyst is well-known. Hydrogenation offers the easiest route for removal of 4-carboxybenzaldehyde (4-CBA) impurity from the crude terephthalic acid (TA). This invention is directed to an improved process for the hydrogenation of crude terephthalic acid in the presence of a catalyst prepared by utilizing palladium metal deposited upon an active carbon support from an organic solution of a palladium salt which reacts with the carbon to produce a catalyst of improved activity and/or selectivity in hydrogenating 4-carboxybenzaldehyde to toluic acid.

Catalysts comprising a Group VIII metal of the Periodic Table of Elements upon an inert carrier are known for use in various hydrogenation reactions. They are usually prepared by impregnating a support material with a solution of a compound of a Group VIII metal and reducing the impregnated commpound to the metal. Catalyst improvements typically have been directed to obtaining increased hydrogenation activity rather than increased activity and/or selectivity in hydrogenating specific compounds.

It is an object of the instant invention to provide an improved method for preparing a catalyst compound of a Group VIII metal. A particular object is to provide a method for preparing such catalysts having increased catalytic activity and/or selectivity in reduction of 4-carboxybenzaldehyde. Another object is to provide a catalytic composition which comprises crystallites of catalytically-active palladium upon the surface of a porous support material wherein a catalyst of improved activity and/or selectivity is obtained for use in a process for reduction of 4-carboxybenzaldehyde in purification of crude terephthalic acid containing up to 10,000 ppm of 4-carboxybenzaldehyde. Still further objects will be apparent from the following specification.

The field of this invention accordingly relates to Group VIII metal catalysts for hydrogenation and purification of terephthalic acid suitable for polyester polymers and copolymers useful in the manufacture of textile fibers. These polymers and copolymers have been made by condensing terephtahalic acid with ethylene glycol and other dihydric alcohols.

As with other supported catalysts, the activity and selectivity of a Group VIII metal catalyst upon a carrier depends on numerous factors such as the amount of Group VIII metal or metals present in the catalyst, the type of support, the method by which the Group VIII metal or metals are deposited and the distribution of the metal or metals on the support.

Such Group VIII catalysts are limited in their ability to selectively hydrogenate impurities in the terephthalic acid, especially 4-carboxybenzaldehyde. Users of terephthalic acid, such as textile fiber manufacturers, often put a rigorous limitation on the allowable concentration of 4-carboxybenzaldehyde in terephthalic acid.

Group VIII metal catalysts, such as palladium catalysts, often are prepared by causing a Group VIII metal salt, such as a palladium salt, to be adsorbed from a solution onto a carrier. In one procedure as is taught in U.S. Pat. No 2,857,337, the salt is thereupon treated with a water-soluble metal hydroxide or basic carbonate which is thereafter reduced to metallic palladium by reducing agents such as formaldehyde, glucose, hydrazine, glycerine and the like. Other conventional methods of preparing palladium catalysts have been taught. U.S. Pat. No. 2,802,794 teaches impregnation of an activated alumina support material with a solution of a compound of the platinum metal group and reducing the impregnated compound to the metal. The preconditioned activated alumina is obtained by heating a hydrated alumina to a temperature of up to 800° C. whereby a microporous alumina is obtained.

U.S. Pat. No. 3,138,560 to Keith, et al., teaches that when sodium tetrachloropalladate or palladium chloride is added to many carbon supports, most of the palladium is immediately deposited as a shiny film of metallic palladium. catalysts so prepared generally have low activities and it has been theorized that the palladium compound is directly reduced to palladium metal by the presence of functional groups, such as aldehydes or free electrons on the carbon surface. Palladium catalysts are accordingly taught as advantageously prepared by fixing the palladium as an insoluble compound prior to reduction to avoid the problems of migration and crystallite growth which can occur when a metal is reduced from solution. Keith '560 teaches inclusion of an oxidizing agent, such as hydrogen peroxide to hydrolyze the palladium prior to reduction by the carbon, thus obtaining improved palladium dispersion and a highly active catalyst. U.S. Pat. No. 3,288,725 to Aftandilian teaches that catalysts produced by deposition of a transition metal compound upon an inert particulate solid and subsequent reduction often have a disadvantage in that uniform deposition of the transition metal compound upon the surface of the inert particulate is accomplished with great difficulty. Hence, '725 states when the metal compound is reduced, the metal atoms deposited on the surface thereof are not exposed, are therefore not completely reduced and maximum potential catalytic activity is not achieved. Aftandilian '725 teaches that reaction of the metal compound with a particulate surface having a suitable hydroxyl group content, followed by reduction with a borohydride, produces an improved catalyst. U.S. Pat. No. 3,737,395 to Arnold, et al., teaches a process for preparing a catalyst which avoids formation of gels which cause lower activity. The catalysts are taught as having uniform and controlled deposition of palladium or platinum and a metallic promoter onto particulate carbon. An aqueous slurry is formed of the palladium or platinum compound and the water soluble metallic promoter. A precipitant is then added to precipitate the palladium or platinum and the metallic promoter, followed by co-reduction of both with a mild reducing agent such as formaldehyde, hydrazine, sodium formate, glucose or hydrogen. U.S. Pat. No. 3,271,327 to McEvoy, et al., teaches a process for depositing palladium upon the surface of a nonporous support material wherein the palladium forms a thin, firm and adherent coating, thus obtaining maximum catalytic activity by means of a thin, peripheral distribution of palladium oxide in the support material. U.S. Pat. No. 3,328,465 to Spiegler teaches the preparation of palladium metal deposited on nonporous carbon support admixed with a porous carbon. The resulting catalyst activity is taught as permitting a rate of hydrogenation about twice that of a hydrogenation process using the same amount of palladium deposited on a nonporous carbon. Previously, carbon used for support of palladium had been mainly porous carbon of vegetable or animal origin. Due to the high porosity of the carbon, some of the palladium became trapped in the pores and did not contribute to the activity of the catalyst. Another disadvantage was that such porous catalysts became fouled with the products of hydrogenation. By dilution of the nonporous carbon with porous carbon, the catalyst metal is distributed throughout the total carbon without plugging the pores of the porous carbon.

U.S. Pat. No. 3,953,369 to Ohara, et al., teaches a method for making a platinum catalyst wherein a high molecular weight surfactant is added to prevent penetration into pores of the support and thus obtain higher catalytic activity.

U.S. Pat. No. 4,256,609 to Dale, et al., teaches a method of making a catalyst of increased activity which comprises physically adsorbing a substance providing a catalytically-active metal of Groups VI, VII and VIII of the Periodic Table into a microporous support by contacting the support with a solution of the substance in a solvent which is a mixture of water and an organic liquid which reduces the surface tension of the solution. Use of an organic liquid alone gives unsatisfactory results according to Example 4E of Dale, '609. Deposition upon the support is obtained by evaporating at least part of the solvent, which can be methanol, ethanol, dioxane, furan, other alcohols and cyclic ethers. The catalytically-active material is deposited in the micropores by physical adsorption instead of ion exchange. The support material can be any material having a microporous structure such as carbon, e.g., coconut charcoal, but is preferably a zeolite of the A, X, and Y series.

The impurities in crude terephthalic acid prepared by oxidation of p-xylene are partially-oxidized products such as toluic acid and 4-carboxybenzaldehyde. These impurities usually are present in significant amounts. Toluic acid is not a particularly harmful impurity in that it is readily removed by cooling and crystallizing terephthalic acid solutions containing it. Other impurities and particularly 4-carboxybenzaldehyde are more difficult to remove from terephthalic acid as such. Purification of crude terephthalic acid containing a high concentration of 4-carboxybenzaldehyde (4-CBA) is usually accomplished by converting 4-CBA by hydrogenation over a catalyst to products which can be easily separated from the terephthalic acid by crystallization. However, only with great difficulty can the level of 4-CBA be reduced to levels below the limitation required by textile manufacturers. 4-Carboxybenzaldehyde is a particularly undesirable impurity because it acts as a chain-stopper during polyesterification of terephthalic acid.

Accordingly, a catalyst and process are highly desirable whereby impurities in crude terephthalic acid, such as 4-carboxybenzaldehyde, are hydrogenated to very low levels by selective reduction to readily separable compounds.

A number of techniques and processes have been developed to purify terephthalic acid by hydrogenation using palladium or platinum catalysts conventionally prepared as described above. Various devices are utilized to obtain the desired selectivity and activity in hydrogenating 4-carboxybenzaldehyde.

U.S. Pat. No. 3,522,298 to Bryant, et al., teaches a process wherein crude terephthalic acid is admixed with an inert gaseous carrier such as steam. The vapor mixture is contacted at a temperature of from 600° to 1000° F. with hydrogen in the presence of a catalyst such as a Group VIII metal upon a carbonaceous support, i.e., palladium upon powdered carbon. Vaporized terephthalic acid is separated by condensation from other constituents in the vapor, e.g., steam, and other impurities. U.S. Pat. No. 3,542,863 to Zimmerschied teaches that hot formic acid treatment of a palladium metal on charcoal catalyst controls the activity and/or reactivity in instances where initial activity of a fresh catalyst is excessive and causes over-hydrogenation of aromatic rings or carboxylic acid groups or where catalysts have become deactivated due to use with oxygenated hydrocarbons. U.S. Pat. No. 3,584,039 to Meyer teaches purification of terephthalic acid by hydrogenation in aqueous liquid phase upon a Group VIII metal on carbon in the presence of hydrogen followed by crystallization from the mother liquor. U.S. Pat. No. 3,591,629 to Stancell, et al., teaches that a phenylbenzene treated catalyst of a Group VIII metal on activated carbon particles minimizes the conversion of terephthalic acid in the presence of hydrogen while effecting high conversions of 4-carboxybenzaldehyde contaminating the commercial acid. U.S. Pat. No. 3,607,921 to Stancell teaches that contact of crude terephthalic acid with carbon monoxide in the presence of palladium on carbon support effects a high percentage conversion of 4-carboxybenzaldehyde contaminating the acid. Surface area of the metal upon the carbon support is taught as being extremely high, to 120 square meters per gram. U.S. Pat. No. 3,726,915 to Pohlmann teaches that copper based on palladium in palladium/carbon catalysts increases the activity of palladium/carbon catalysts in hydrogenation of 4-carboxybenzaldehyde. U.S. Pat. No. 3,799,976 to Nienburg, et al., teaches purification of terephthalic acid containing 4-carboxybenzaldehyde by heating an aqueous mixture of the crude acid with formic acid in contact with a Group VIII metal as catalyst. U.S. Pat. No. 4,260,817 to Thompson, et al., teaches a method for purifying crude terephthalic acid by hydrogenating the crude acid to make toluic acid from 4-carboxybenzaldehyde and p-xylene from terephthalyl dialdehyde wherein the reduction takes place in two stages, the aldehyde radical forming an alcohol radical and in turn forming a methyl radical. The catalyst comprises two Group VIII metals on carbon particles.

Accordingly, it is well-known that crude terephthalic acid containing 4-carboxybenzaldehyde and other impurities can be purified by hydrogenation over a conventionally prepared Group VIII metal on carbon catalyst. However, more selective catalysts and processes are highly desirable wherein crude terephthalic acid containing high levels of 4-carboxybenzaldehyde is selectively hydrogenated to contain very low levels of 4-carboxybenzaldehyde.

SUMMARY

A catalyst and process for producing a purified terephthalic acid wherein 4-carboxybenzaldehyde content is reduced to very low levels, to less than 100 parts per million in a standard laboratory evaluation, which comprises reacting in liquid phase a mixture of hydrogen and crude terephthalic acid at a temperature of from about 100° C. to about 300° C. and a pressure from about 200 to about 1,500 psi in the presence of a catalyst compound comprising palladium crystallites adsorbed upon a porous activated carbonaceous support wherein the catalyst is prepared by contacting a solution of a suitable palladium salt in an organic solvent, in the absence of hydrogen, with a suitable activated carbon, such as coconut charcoal, wherein the palladium salt is reduced to palladium metal crystallites by the activated support, palladium content is not greater than 0.6 (wt) % and said crystallites are predominantly less than 35Å in longitudinal measurement.

DETAILED DESCRIPTION OF THE INVENTION

The process of the instant invention relates to purification of terephthalic acid wherein 4-carboxybenzaldehyde (4-CBA) content is reduced to very low levels, to less than 100 parts per million (ppm) in a standard laboratory test. The general method requires use of a palladium catalyst prepared from a palladium salt, such as palladium nitrate, which dissolves in organic solvents such as methanol, ethyl acetate, methyl ethyl ketone, etc. The organic solution of the palladium salt is contacted with the activated carbonaceous support materials. The palladium reacts with the activated carbonaceous support material and is thereupon deposited on the carbon. The organic solvent is inert to the carbonaceous support material.

It has been found that catalysts prepared by the above method are effective in purifying crude terephthalic acid. Moreover, the palladium on carbon catalyst is selective in reducing 4-carboxybenzaldehyde to very low levels.

The activated porous carbonaceous support or substrate is any suitable granular activated carbon having a surface area of at least 600 m$^2$/g (N$_2$, BET method). Activated carbon granules of high surface area prepared from plant, animal or mineral sources can be used. While activated carbon granules are preferred, the method of this invention would also extend to activated carbon used in the form of pellets and other particulate forms. Preferably the substrate is activated carbon of plant or animal origin, most preferably of coconut charcoal. It is essential that the porous carbonaceous support be in an activated state whereby it reacts on contact with the palladium salt to reduce the palladium salt to palladium metal crystallites. Other reducing agents, such as hydrogen, are not suitable and are not present.

The palladium catalyst of this invention is prepared from soluble salts of palladium in an organic solvent which contains up to 24 carbon atoms wherein the palladium salt reacts with the activated surface of a porous carbonaceous support, such as activated carbon, in the presence of the organic solvent over a period of from 1 to 24 hours without significant evaporation of the solvent. The resulting composition comprising the palladium on the support, i.e., activated carbon, is washed, filtered and dried. The catalyst can be used immediately for terephathalic acid purification.

It is essential that the palladium crystallites on the surface, and those contained within the carbonaceous support, be predominantly less than 35Å in longitudinal measurement, preferably all said palladium crystallites are less than 35Å in longitudinal measurement. Accordingly, it is essential that other reducing agents, such as hydrogen, not be used in the preparation of the palladium on the activated carbonaceous support because use of hydrogen causes the palladium crystallites to increase in size to greater than 35Å in longitudinal measurement and to decrease the palladium surface area on the surface of the carbonaceous support. The increased palladium crystallite size of above 35Å results in lower palladium surface area and in lower activity of the palladium on carbon catalyst in hydrogenating 4-carboxylbenzaldehyde.

To standardize test procedures and to determine the detrimental effect of hydrogen reduction on the invented catalyst, before a laboratory evaluation of the catalyst activity, a water slurry of the freshly-prepared catalyst was first heated under hydrogen for a period of about 1¾ to 2 hours at a temperature of 270° C. After the composition was cooled, the catalyst particles were filtered from the water slurry and dried under vacuum at approximately 80° C.

The catalysts of the process of the instant invention comprise palladium crystallites predominantly less than 35Å in longitudinal measurement upon a support of carbonaceous material of plant origin or animal origin.

For reasons which are not understood, it has been found that the preparation of a catalyst comprising palladium upon a porous activated carbonaceous support and deposited from an organic solution of palladium nitrate so as to react with the activated support resulted in catalytically-active palladium crystallites predominantly of less than 35 angstrom units (Å) in longitudinal measurement as indicated by X-ray diffraction analysis. Only crystallites with a longitudinal measurement larger than 35Å can be detected due to the limit of resolution by the X-ray diffraction apparatus.

For reasons which are not understood, it has been found that hydrogenation of crude terephthalic acid with a catalyst comprising palladium deposited upon and reacted with a porous activated carbonaceous support from an organic solution of palladium nitrate gives a better reduction of 4-carboxybenzaldehyde (4-CBA) with decreasing palladium content of the catalyst in the 0.1 (wt)% to 0.6 (wt)% range. Preferably, the catalyst should have less than 0.3 (wt)% palladium content. This is also an economic advantage because less palladium is needed.

It has been found that use of a palladium salt in an organic solvent which is added to a porous activated support material in preparation of the instant catalyst results in a hydrogenation catalyst which reduces 4-CBA content of crude terephthalic acid to a very low level, below 100 ppm in a standard laboratory test, if less than 0.3 (wt)% of palladium of total catalyst composition weight is deposited. The organic solvent can contain up to 24 carbon atoms and can be an alcohol of from 1 to 12 carbon atoms, a ketone of from 2 to 12 carbon atoms, an ester of from 2 to 20 carbon atoms, an aromatic hydrocarbon of from 6 to 24 carbon atoms or a chlorinated aliphatic hydrocarbon of up to 12 carbon atoms. Typical examples are methanol, ethanol, ethyl acetate, 2-butanone, methyl ethyl ketone, diethyl ketone, acetone, etc. Preferred organic solvents are short-chain alcohols such as methanol, ethanol, propanol, n-butanol and isobutanols, short-chain esters such as ethyl acetates and ketones such as acetone and 2-butanone. Mixtures of two or more of these organic solvents can also be used. A preferred solvent is 2-butanone.

Solubility of the palladium salt is a practical consideration. While palladium nitrate was found to have reasonably good organic solubility for the instant invention, any other soluble palladium salt can also be suitable in combination with a limited number of solvents.

Suitable other palladium salts are palladium chloride, palladium bromide, palladium acetate, etc.

The distribution state of the deposited palladium metal in the catalyst prepared according to the process of this invention can be determined according to electron microprobe analysis in a Phillips AMR/3 electron microprobe. The figure illustrates the results of electron microprobe analysis (EMPA) of catalyst granules of the instant invention wherein surface deposition of palladium is demonstrated.

Surface area of supported metallic palladium can be calculated from X-ray diffraction data. Alternatively, the surface area of the palladium metal deposited on porous carbonaceous material can be calculated from carbon monoxide adsorption measurements. Palladium surface area of fresh catalysts of the present invention can be as high as 230 m$^2$/g of palladium, or even higher, as determined by either method.

A method has also been discovered of preparing supported metallic palladium whose crystallites are predominantly less than 35Å in longitudinal measurement. This method consists of depositing a reducible salt of palladium upon solid supporting granules of activated carbon from solution in an organic solvent, wherein the activated granules react with the reducible salt of palladium to reduce the palladium salt to metallic palladium crystallites of less than 35Å in longitudinal measurement.

Palladium uptake by carbon granules, using the method of preparing the instant catalyst, usually results in metallic palladium particles of less than 0.6 (wt)% of total catalyst weight, preferably less than 0.30 (wt)% of total catalyst weight. Higher concentrations are of little avail because in the process of reducing 4-CBA to removable impurities, higher concentrations of palladium metal on the catalyst do little to improve the efficiency of the catalyst. On the contrary, higher concentrations appear to be harmful.

The palladium salt preferably utilized in the present invention is palladium nitrate dissolved in organic solvent. The nitrate solution is then added to a mixture of the organic solvent and the activated carbon. Other soluble salts, such as halides, etc., can also be used.

In preparation of the instant invented catalyst, granular activated vegetable carbon can be washed with the solvent to remove carbon fines, but this step is not necessary. The washed vegetable carbon is then added to the organic solvent. The resulting mixture is kept under agitation. The palladium nitrate in solution of the same organic solvent is thereupon added to the charcoal solution. The resulting mixture is kept under agitation at a temperature below the boiling point of the solvent, conveniently at room temperature, for a period of from 1 to 24 hours. The resulting catalyst particles are filtered from the mixture after addition of water to the mixture, washed with water at a temperature of from 0° to 50° C., and dried under vacuum of 100 mm Hg, and temperature of 80° C. for a period of up to 16 hours. It should be noted that air-drying of the catalyst without water washing may result in solvent explosion.

The catalyst prepared in this method is ready for use for terephthalic acid purification. To standardize the catalyst evaluation, to determine the detrimental effect of hydrogen reduction upon the invented catalyst and consequent effect on catalyst life, and to avoid measurement of a possible misleading initial catalyst activity, the catalyst is treated in water with hydrogen at temperatures of 270° C. The catalyst particles are added to water in an autoclave, and hydrogen gas is introduced under pressure into the autoclave. The mixture of catalyst particles, hydrogen gas and water is heated to a temperature of 270° C. for a period of about 1¾ to 2 hours. The mixture is then cooled.

The activity and selectivity of each catalyst prepared by this method was evaluated thereupon under standard laboratory conditions which simulated purification of terephthalic acid from the 4-carboxybenzaldehyde impurity under full-scale plant process conditions. 4-Carboxybenzaldehyde content of a terephthalic acid plant process stream can vary widely. Standard laboratory test conditions, accordingly, were used to measure activity and selectivity of catalyst compositions of the instant invention.

In summary, the instant invention comprises a method of preparing a catalyst composition and a catalytic hydrogenation process for hydrogenating crude terephthalic acid containing up to 10,000 ppm of 4-carboxybenzaldehyde in the presence of the catalyst composition, water and hydrogen at a temperature of from about 100° C. to about 300° C. and a pressure of from about 200 to 1500 psig, and recovering purified terephthalic acid from the mixture. The catalyst is prepared by contacting porous activated carbonaceous support granules with a palladium salt in the presence of an organic solvent, wherein the palladium salt reacts with the activated support to reduce the palladium salt to palladium metal crystallites, the palladium content on said granules being not greater than 0.6 (wt)%, wherein the organic solvent can contain up to 24 carbon atoms and is selected from the group consisting of an alcohol, a ketone, an ester, a hydrocarbon and a chlorinated hydrocarbon. The palladium soluble salt is selected from the group consisting of palladium nitrate, palladium chloride, palladium diacetate, etc. Palladium nitrate is preferred. The activated porous support is preferably an activated carbon having a high surface area of at least 600 m$^2$/g (N$_2$, BET method). The preferred solvents are short-chain alcohols such as methanol, ethanol, propanol, n-butanol; and isobutanol; short-chain esters such as ethyl acetate and ketones such as acetone and butanone. A preferred solvent is 2-butanone.

The invention will be further illustrated by reference to the following specific examples.

EXAMPLE I

A catalyst was prepared in the method of the instant invention. Granular activated coconut charcoal (12.0 g), of 4 to 8 mesh, was washed with methanol to remove the carbon fines. The methanol was decanted and the wet charcoal was transferred into a 3-necked, 300-ml flask. Methanol (40 ml) was placed over it and stirred with a paddle, located in the methanol layer above the carbon, and cooled to 5° C. From a dropping funnel, a freshly-prepared solution of Pd(NO$_3$)$_2$ (0.150 g) in methanol (50 ml) was introduced dropwise in 5 to 10 minutes and stirred for one hour without significant evaporation of the methanol solvent. Then water was added before filtration to avoid the possibility of an explosion.

The prepared catalyst was then analyzed by X-ray diffraction to assay the palladium content in (wt)%. Palladium crystallites were present on the carbon granules.

Analytical results were as follows:

| | |
|---|---|
| Palladium Uptake From Palladium Solution - (wt) % (Based on Palladium Material Balance) | 102 |
| Palladium Crystallites >35Å - Contained on Carbon Granules - (wt) % | 9 |
| <35Å - Contained on Carbon Granules - (wt) % | 91 |
| Palladium Surface Area | |
| ($m^2$/g of Catalyst) | 0.98 |
| ($m^2$/g Palladium) | 306 |

The above analytical results positively indicated that palladium crystallites were present upon the catalyst support. Because crystallites smaller than 35Å are not detectable by XRD analysis, the rest of the palladium calculated from the material balance, 91(wt)%, of the total palladium was present as small <35Å crystallites. The above catalysts were prepared in the absence of hydrogen.

Freshly-prepared samples of the prepared catalyst were thereupon aged to standardize the catalyst evaluation and to avoid measurement of possibly misleading catalyst activity. The freshly-prepared catalyst was treated in distilled water (180 ml) and hydrogen gas (200 psig) in a rocking autoclave at 270° C. for 1¾ to 2 hours. The mixture was then cooled. Polarographic analysis of the catalyst indicated that the effect of hydrogen treatment during the "aging" procedure was to increase the palladium crystallites in size and to decrease the palladium surface area on the surface of the carbon granules. Palladium assay, by X-ray diffraction, of palladium content of the carbon granules indicated palladium content remained constant, i.e., the aging process did not affect palladium content.

The aged catalyst was then evaluated in a standardized laboratory batch purification of crude terephthalic acid.

Crude terephthalic acid (TA) (12.9 g), distilled water (150 ml), catalyst (0.17 g) and hydrogen gas (200 psig) were charged into a 300-ml rocking autoclave. The rocker was started (47 rpm), and heated to 250° C. in approximately 45 minutes. Rocking was continued at 250° C. for 1½ hours. Then the heater and rocker were turned off and the mixture cooled overnight. The purified terephthalic acid (PTA) crystals and catalyst granules were filtered on a coarse, sintered glass filter, were washed with 100 ml distilled water, and dried in a vacuum oven at 105° C. for 16–18 hours. The catalyst granules were separated with a forceps.

The resulting PTA was analyzed for impurities. The 4-carboxybenzaldehyde (4-CBA) was determined by polarographic analysis. The other impurities were determined, after estrification, by liquid chromatography. The contribution of these contaminants to the visible fluorescence of the sample was determined as the "relative fluorescence contribution" (RFC) and defined as the total peak area of all fluorescent impurities relative to a fluorescent internal standard.

The aged catalyst, after the batch evaluation, was then aged in a second aging procedure and again analyzed and evaluated.

The second aging procedure again increased the size of the palladium crystallites and decreased the palladium surface area on the surface of the carbon granules. The increase in palladium crystallite size, to sizes greater than 35Å, decreased the activity of the catalyst in reducing 4-CBA content of the crude terephthalic acid. Details are in Table I.

TABLE I

Preparation And Evaluation of Palladium On Carbon Catalysts

| Run No. | Pd Uptake (wt) % | State | Pd Assay (wt) % X-RD | Pd Content % of Total Pd >35A | <35A | Pd Surface Area[a] ($m^2$/g) |
|---|---|---|---|---|---|---|
| Preparation | | | | | | |
| 4761-60-1 | 102 | Fresh | 0.32 | 9 | 91 | 0.98 |
| 4761-110-1 | 102 | Aged | 0.36 | 32 | 68 | 0.44 |
| 4761-169-1 | 102 | 2 × Aged | 0.34 | 53 | 47 | 0.35 |
| Evaluation | | | | Impurities in PTA[b] | | |
| | | | | 4-CBA (ppm) | | RFC |
| 4761-60-1 | | Fresh | | 136 | | — |
| 4761-110-1 | | Aged | | 190 | | 68 |
| 4761-169 | | 2 × Aged | | 240 | | — |

[a]Surface area of palladium in sq. meters/gram of catalyst.
[b]Crude terephthalic acid had 7900 ppm 4-carboxybenzaldehyde and 1460 ppm p-toluic acid.

EXAMPLE II

The above data indicate that as percent of total palladium content greater than 35Å in longitudinal measurement increased, the efficiency of the catalyst decreased, as measured by the increase in 4-CBA impurities in purified terephthalic acid.

A number of catalysts were prepared to illustrate the present invention. In all cases approximately 4 to 8 mesh granular activated carbons of coconut shell origin were used. Occasionally, but not always, they were washed with the solvent in question, or distilled water, to to remove fines and then drained. The activated carbons were contacted with the organic solution of palladium nitrate, as indicated below, washed, drained and dried at a temperature of approximately 80° C. It was noted that the interaction of organic solvents with the activated carbon was exothermic. Cooling was used.

Catalyst A. Granular activated coconut charcoal (18 g) was washed with distilled water to remove the carbon fines. The water was decanted and the moist charcoal was transferred into a 3-necked, 300-ml flask. It was cooled in an ice-bath. Distilled water (60 ml) and concentrated (70%) nitric acid (1.5 ml) were placed over it. A glass stirrer was installed which had a small paddle immersed into the water layer above the carbon. The stirrer was turned on. Palladium nitrate (0.234 g) was dissolved in a mixture of distilled water (36.0 ml) and concentrated (70%) nitric acid (1.5 ml). This solution was added drop-wise from a dropping funnel to the stirred charcoal-water mixture in 6 minutes with intense agitation. The stirring was continued for 17 hours. Then, the catalyst was filtered, washed with distilled water and dried in vacuum at 80° C. Palladium on carbon was 0.53 (wt)%.

Catalyst B. Granular activated coconut charcoal (12.0 g) was washed with methanol to remove the carbon fines. The methanol was decanted and the wet charcoal was transferred into a 3-neck, 300-ml flask. Methanol (40 ml) was placed over it and stirred with a paddle located in the methanol layer above the activated carbon, and cooled to 5° C. From a dropping funnel, a solution of Pd(NO₃)₂ (0.150 g) in methanol (50 ml) was introduced drop-wise in 6 minutes and stirred for 21 hours without significant evaporation of the methanol solvent. Then, water was added and the catalyst was filtered, washed with distilled water, and dried in vacuum at 80° C. Water was added before filtration to avoid possibility of an explosion. Palladium on carbon was 0.52 (wt)%.

Catalyst C. In the method of Catalyst B, Catalyst C was prepared. The amounts of reagents were changed. To activated coconut charcoal (18.0 g) under methanol (50.0 ml) at 5° C., was added a solution of: Pd(NO₃)₂ (0.143 g) in methanol (60 ml). Palladium on carbon was 0.19 (wt)%.

Catalyst D. In the method of Catalyst B, a solution of Pd(NO₃)₂ (0.080 g), in methanol (60 ml) was used. Palladium on carbon was 0.15 (wt)%.

Catalyst E. In the method of Catalyst B, the methanol was replaced by ethyl acetate, Catalyst E was prepared from Pd(NO₃)₂ and ethyl acetate as follows: Pd(NO₃)₂ (0.156 g), ethyl acetate (25 ml). Palladium on carbon was 0.33 (wt)%. The carbon was not washed with the solvent prior to the catalyst preparation.

Catalyst F. In the method of Catalyst E, Catalyst F was prepared from Pd(NO₃)₂ dissolved in ethyl acetate as follows: Pd(NO₃)₂ (0.064 g), and ethyl acetate (25 ml). Palladium on carbon was 0.18 (wt)%.

Catalyst G. In the method of Catalyst E, Catalyst G was prepared from Pd(NO₃)₂ dissolved in ethyl acetate as follows: Pd(NO₃)₂ (0.036 g), ethyl acetate (25 ml). Palladium on carbon was 0.07 (wt)%.

Catalyst H. In the method of Catalyst B, the methanol was replaced by 2-butanone, Catalyst H was prepared. 2-Butanone was poured over coconut charcoal (12.0 g), cooled, and slowly a solution of Pd(NO₃)₂ (0.156 g) in 2-butanone (25 ml) was added. Palladium on carbon was 0.39 (wt)%.

Catalyst I. In the method of Catalyst H, Catalyst I was prepared from Pd(NO₃)₂ in 2-butanone as follows: Pd(NO₃)₂ (0.064 g), 2-butanone (25 ml). Palladium on carbon was 0.16 (wt)%.

Before evaluation, the catalysts were hydrogenated at 270° C.

Distilled water (150 ml), the catalyst (2 to 20 g) and hydrogen gas at 200 psig were charged into a 300-ml rocking autoclave, heated to 270° C. and held at temperature for 1¾ hours. After cooling, the catalyst was recovered and dried in a vacuum oven at 80° C.

In a simulation of a plant hydrogenation process, the above catalysts were evaluated for terephthalic acid (TA) purification in a standard laboratory test. Catalyst and crude terephthalic acid were charged into a 300-ml rocking autoclave as follows: 12.9 g of crude TA, containing 7900 ppm 4-carboxybenzaldehyde (4-CBA): 150 ml distilled water; 0.17 g of catalyst under evaluation and; 200 psig hydrogen gas. The reactor was heated to 250° C. and held at that temperature for 3½ hours. After cooling, the TA crystals were filtered, washed with 100 ml distilled water and dried in vacuum at 105° C. The purified TA was analyzed by liquid chromatography and by polarography. Results are in Table II. A commercially available palladium/carbon catalyst was used as a comparative example.

TABLE II

| Catalyst Characterizations and Evaluations[a] | | | | | |
|---|---|---|---|---|---|
| Catalyst and Run No. | Catalyst Precursor and Solvent | Pd on C (wt) % | Surface Area m²/g [b] [c] | Pd >35 Å %[d] | 4-CBA ppm |
| Commercial | Unknown | 0.50 | 0.54 108 | 68 | 153 |
| A 5054-16-1 | Pd(NO₃)₂ (HNO₃) | 0.53 | — — | 25 | 311 |
| B 4761-110-1 | Pd(NO₃)₂ (Methanol) | 0.52 | 0.44 85 | 32 | 190 |
| C 4761-156-1 | Pd(NO₃)₂ (Methanol) | 0.19 | — — | 0 | 23 |
| D 4761-88-1 | Pd(NO₃)₂ (Methanol) | 0.15 | 0.30 200 | 0 | 87 |
| E 5054-37-1 | Pd(NO₃)₂ (Ethyl Acetate) | 0.33 | 0.46 139 | 0 | 306 |
| F 5054-86-1 | Pd(NO₃)₂ (Ethyl Acetate) | 0.18 | — — | — | 150 |
| G 5054-146-1 | Pd(NO₃)₂ (Ethyl Acetate) | 0.07 | 0.11 157 | 0 | 58 |
| H 5054-41-1 | Pd(NO₃)₂ (2-Butanone) | 0.39 | 0.80 205 | 0 | 98 |
| I 5054-145-1 | Pd(NO₃)₂ (2-Butanone) | 0.16 | 0.22 138 | 0 | 52 |

Notes:
[a] The crude terephthalic acid used in the catalyst evaluation runs had 7900 ppm 4-carboxybenzaldehyde and 1460 ppm p-toluic acid content.
[b] Surface area of palladium in sq. meters/gram of catalyst after heat treatment in hydrogen at 270° C.
[c] Surface area of palladium in sq. meters/gram of palladium after heat treatment in hydrogen at 270° C.
[d] After hydrogen treatment at 270° C. The size of the palladium crystallites usually increased during the hydrogen treatment at 270° C.

What is claimed is:

1. A method of making a catalyst for selectively hydrogenating 4-carboxybenzaldehyde in purification of terephthalic acid containing up to 10,000 ppm of 4-carboxybenzaldehyde in a standard laboratory test wherein 4-carboxybenzaldehyde content is decreased to less than 100 parts per million which consists essentially of reacting a palladium salt with a porous activated carbonaceous support material to reduce the said palladium salt to palladium metal crystallites, said porous activated carbonaceous support material consisting essentially of activated carbon granules having a surface area of at least 600 m²/g, and said crystallites are predominantly less than 35Å in longitudinal measurement, which method comprises contacting said support in the absence of hydrogen with a non-aqueous solution of a palladium salt in an organic solvent which is inert to said support material and wherein said palladium salt is reduced to palladium metal crystallites by said activated support.

2. The method of claim 1 wherein said palladium salt is selected from the group consisting of palladium nitrate, palladium chloride, palladium bromide and palladium acetate.

3. The method of claim 1 wherein said palladium salt is palladium nitrate.

4. The method of claim 1 wherein said organic solvent contains up to 24 carbon atoms and is selected from the group consisting of an alcohol, a ketone, an ester, an aromatic hydrocarbon and a chlorinated hydrocarbon.

5. The method of claim 1 wherein said organic solvent is selected from the group consisting of methanol, ethanol, propanol, n-butanol, isobutanol, ethyl acetate, acetone and 2-butanone.

6. The method of claim 1 wherein said organic solvent is 2-butanone.

7. The method of claim 1 wherein said activated support material is selected from the group consisting of activated plant-origin carbon, activated animal-origin carbon and activated mineral-origin carbon.

8. The method of claim 7 wherein said plant-origin carbon is activated coconut charcoal.

9. The method of claim 1 wherein catalyst palladium content is less than 0.3 (wt)% of total catalyst weight.

* * * * *

UNITED STATES PATENT OFFICE
CERTIFICATE OF CORRECTION

Patent No. 4,476,242          Dated   October 9, 1984

Inventor(s)   Imre Puskas and Steven A. Cerefice

It is certified that error appears in the above-identified patent and that said Letters Patent are hereby corrected as shown below:

Patent reads:

| Col. | Line | | |
|---|---|---|---|
| 9 | 2 | "Palladium Uptake From    102" and should read | --Palladium Uptake From-- |
| 9 | 3 | "Palladium Solution - (wt) %" and should read | --Palladium Solution - (wt) %   102-- |
| 9 | 5 | "Palladium Crystallites    9" and should read | --Palladium Crystallites-- |
| 9 | 7 | "Carbon Granules - (wt) %" and should read | --Carbon Granules - (wt) %   9-- |
| 9 | 8 | "<35A - Contained on   91" and should read --<35A - Contained on-- | |
| 9 | 9 | "Carbon Granules - (wt) %" and should read | --Carbon Granules - (wt) %   91-- |

Signed and Sealed this

Twelfth   Day of   November 1985

[SEAL]

Attest:

DONALD J. QUIGG

Attesting Officer      Commissioner of Patents and Trademarks